United States Patent
Johnsen et al.

(10) Patent No.: US 8,230,994 B2
(45) Date of Patent: Jul. 31, 2012

(54) CONTAINER FOR HOLDING ENDODONTIC INSTRUMENTS

(75) Inventors: James B. Johnsen, Beaverton, OR (US); Hal J. Oien, Tualatin, OR (US)

(73) Assignee: Jordco, Inc., Beaverton, OR (US)

( * ) Notice: Subject to any disclaimer, the term of this patent is extended or adjusted under 35 U.S.C. 154(b) by 216 days.

(21) Appl. No.: 12/953,243

(22) Filed: Nov. 23, 2010

(65) Prior Publication Data

US 2011/0068031 A1 Mar. 24, 2011

Related U.S. Application Data

(63) Continuation of application No. 11/367,158, filed on Mar. 3, 2006, now abandoned.

(51) Int. Cl.
*B65D 83/10* (2006.01)
(52) U.S. Cl. .......................................... 206/369
(58) Field of Classification Search .................. 206/369, 206/63.5, 368, 370, 363, 438, 779, 775, 777, 206/366, 478; 433/224, 77, 79, 81, 102, 433/72; 510/161; 422/310
See application file for complete search history.

(56) References Cited

U.S. PATENT DOCUMENTS

| | | | | |
|---|---|---|---|---|
| 3,421,679 A | * | 1/1969 | Goldman | 206/523 |
| 4,698,210 A | * | 10/1987 | Solazzi | 356/246 |
| 5,219,525 A | * | 6/1993 | Harrison | 210/359 |
| 5,913,422 A | * | 6/1999 | Cote et al. | 206/370 |
| 6,325,968 B1 | * | 12/2001 | Fricker et al. | 422/28 |

* cited by examiner

*Primary Examiner* — Jacob K Ackun
*Assistant Examiner* — Jenine Pagan
(74) *Attorney, Agent, or Firm* — Kolisch Hartwell, P.C.

(57) ABSTRACT

A container for holding endodontic instruments that may include a base, a foam pad, a retainer, and a lid. The base may include a well with a bottom and sidewalls extending upwardly from the bottom to an open-ended top. The foam pad may be configured to hold one or more endodontic instruments inserted through the pad, and dimensioned to cover the open-ended top of the well. The retainer may be configured to clamp the foam pad over the open-ended top of the well so that the pad is tautly maintained in a holding position, whereby the foam pad is configured to hold at least a portion of an endodontic instrument within the well. The lid may be coupled to the base, and movable between an open position and a closed position that covers the foam pad.

21 Claims, 5 Drawing Sheets

CONTAINER FOR HOLDING ENDODONTIC INSTRUMENTS

CROSS-REFERENCE TO RELATED APPLICATION

This application is a continuation of U.S. patent application Ser. No. 11/367,158, filed Mar. 3, 2006 now abandoned, which is incorporated herein by reference in its entirety for all purposes.

BACKGROUND

During an endodontic procedure, a dental practitioner uses various endodontic instruments to remove infected material from the root canal of a patient's teeth. These instruments come in a range of diameters and/or cone angles, and are sequentially used to bore out the root canal. To facilitate the procedure, the instruments commonly are organized in a manner that enables the dental practitioner to readily access the various instruments, and to differentiate them based on their diameters. The instruments are also sterilized prior to use to reduce and/or prevent the risk of infection.

Endodontic instruments are sometimes stored in containers that enable a practitioner to organize and/or sterilize the instruments prior to a procedure. Examples of containers for holding endodontic instruments are found in U.S. Pat. Nos. 3,092,443; 4,191,291; 4,232,784; 4,253,830; 4,306,862; 4,397,395; 4,503,972; 5,006,066; 5,108,287; 5,154,611; 5,172,810; 5,358,112; 5,525,314; 5,967,778; 6,464,497; 6,681,925; and 6,719,560 the disclosures of which are hereby incorporated by reference in their entirety for all purposes.

DETAILED DESCRIPTION OF THE DEPICTED EMBODIMENTS

Figure 1:
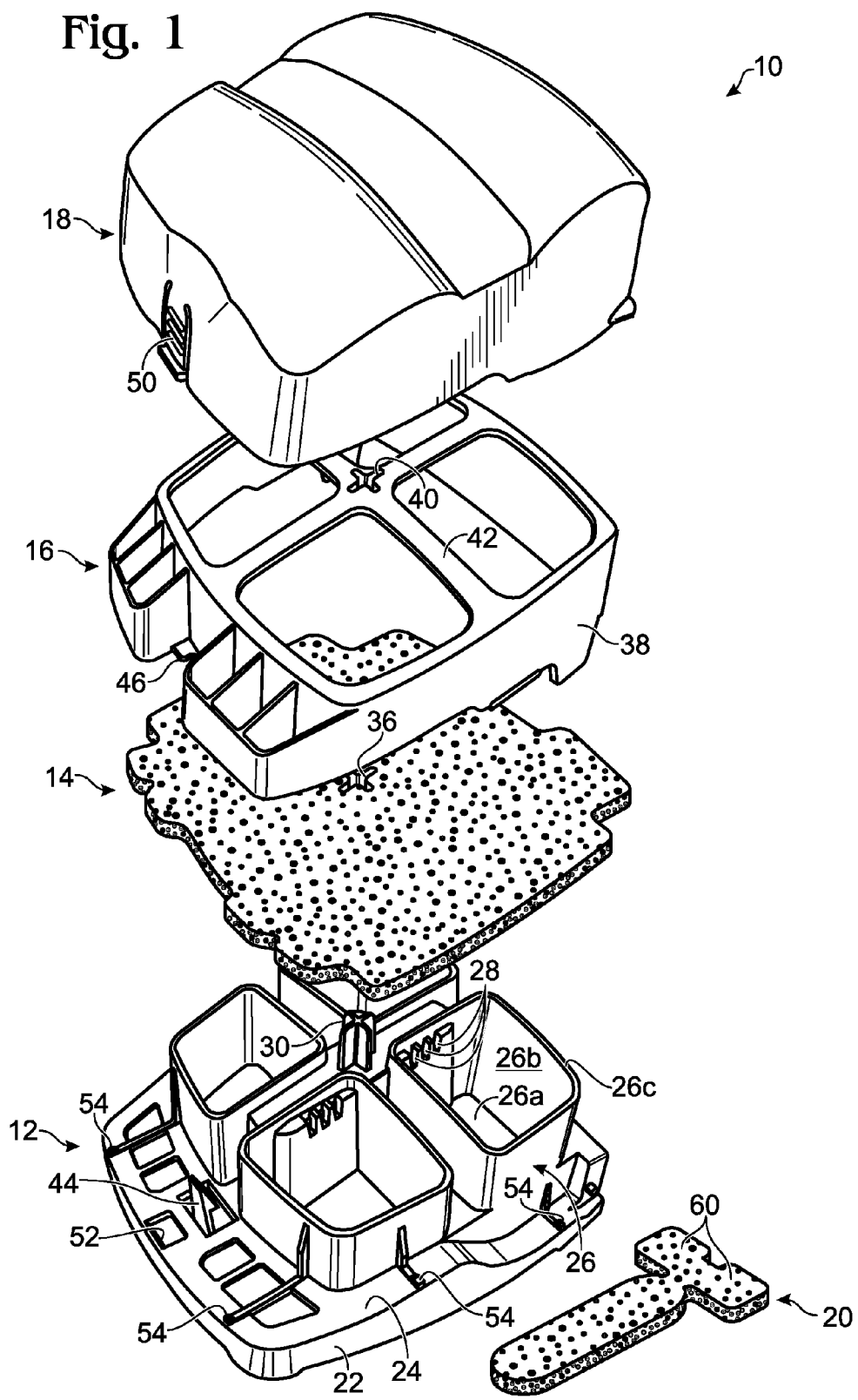
FIG. 1 shows an exploded diagram of a container for holding endodontic instruments, according to aspects of the present disclosure.

FIG. 1 shows an exploded diagram of an embodiment of a container 10 for holding endodontic instruments. The container may include a base 12, a foam pad 14, a retainer 16, a lid 18, and a foam filter 20. The base supports the container on a substantially planar surface, and defines open-ended instrument wells having vents. The foam pad forms a foam barrier over the open-ended tops of the instrument wells, and retains within the instrument wells the boring tips of endodontic instruments that have been inserted through the foam pad for storage and/or sterilization. The retainer tautly clamps the foam pad to the base. The lid is removably coupled to the base, and is movable between an open position and a closed position that covers the foam pad. The foam filter engages the base in a manner that forms a foam barrier between the vents and the space outside the container.

FIG. 1 shows aspects of the base 12, which supports the container on a substantially planar surface, and defines open-ended instrument wells having vents. The base includes substantially vertical supports 22, substantially horizontal supports 24, one or more instrument wells 26, one or more vents 28, and/or a guide 30. The substantially vertical supports 22 support the container on a planar surface. The substantially horizontal supports 24 couple the wells to the vertical supports. The one or more instrument wells 26 each have a bottom 26a and sidewalls 26b extending upwardly from the bottom to an open-ended top. The top edge 26c of the sidewalls form a surface for supporting the foam pad 14. The foam pad in turn forms a foam barrier over the open-ended tops of the instrument wells. As described below, the foam pad retains within the instrument wells the boring tips of endodontic instruments that have been inserted through the foam pad, and allows steam to pass into and out of the wells. The vents 28 provide another passage through which steam passes into and out of the wells. The guide 30 guides the foam pad 14 and/or the retainer 16 into proper orientations for engaging the base.

Figure 2:
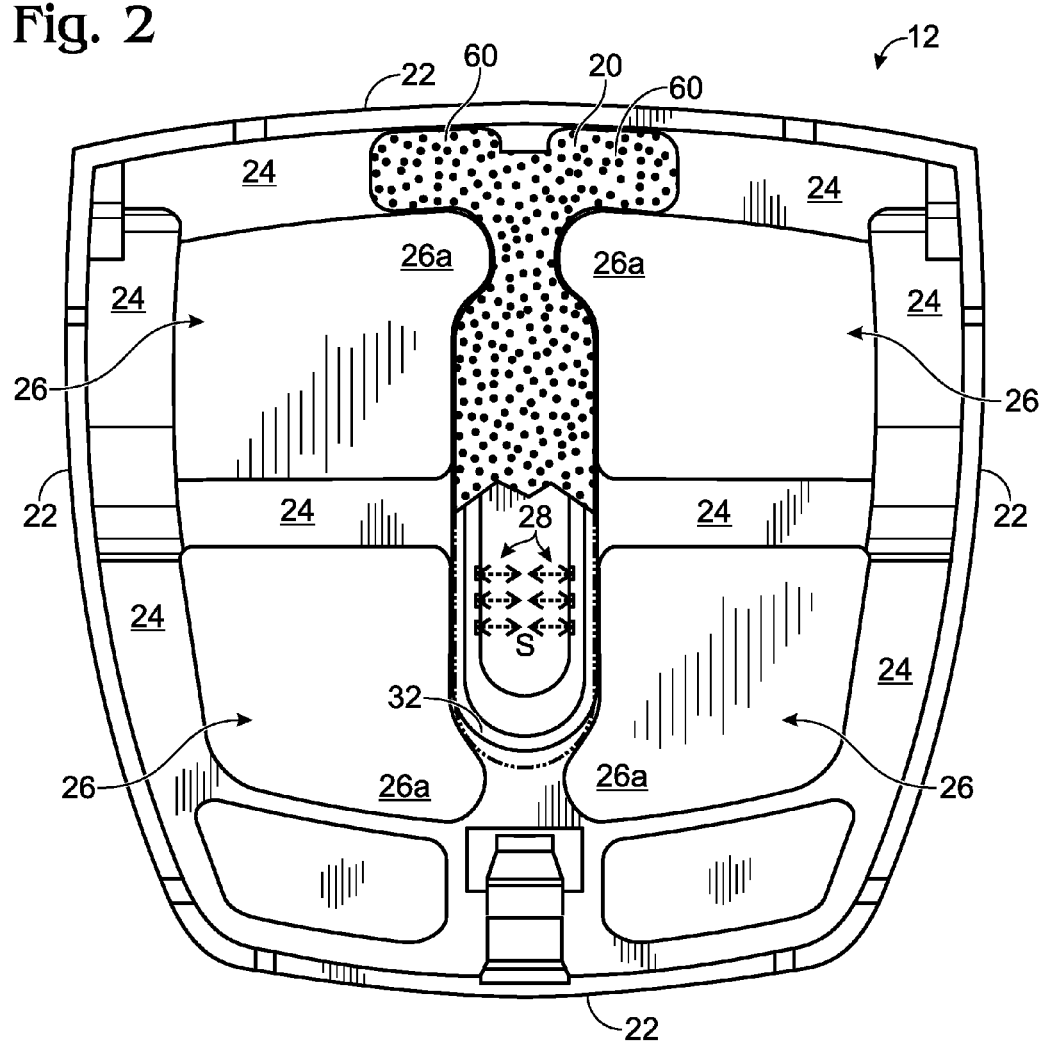
FIG. 2 shows a bottom view of the container for holding endodontic instruments from FIG. 1.
Figure 7:
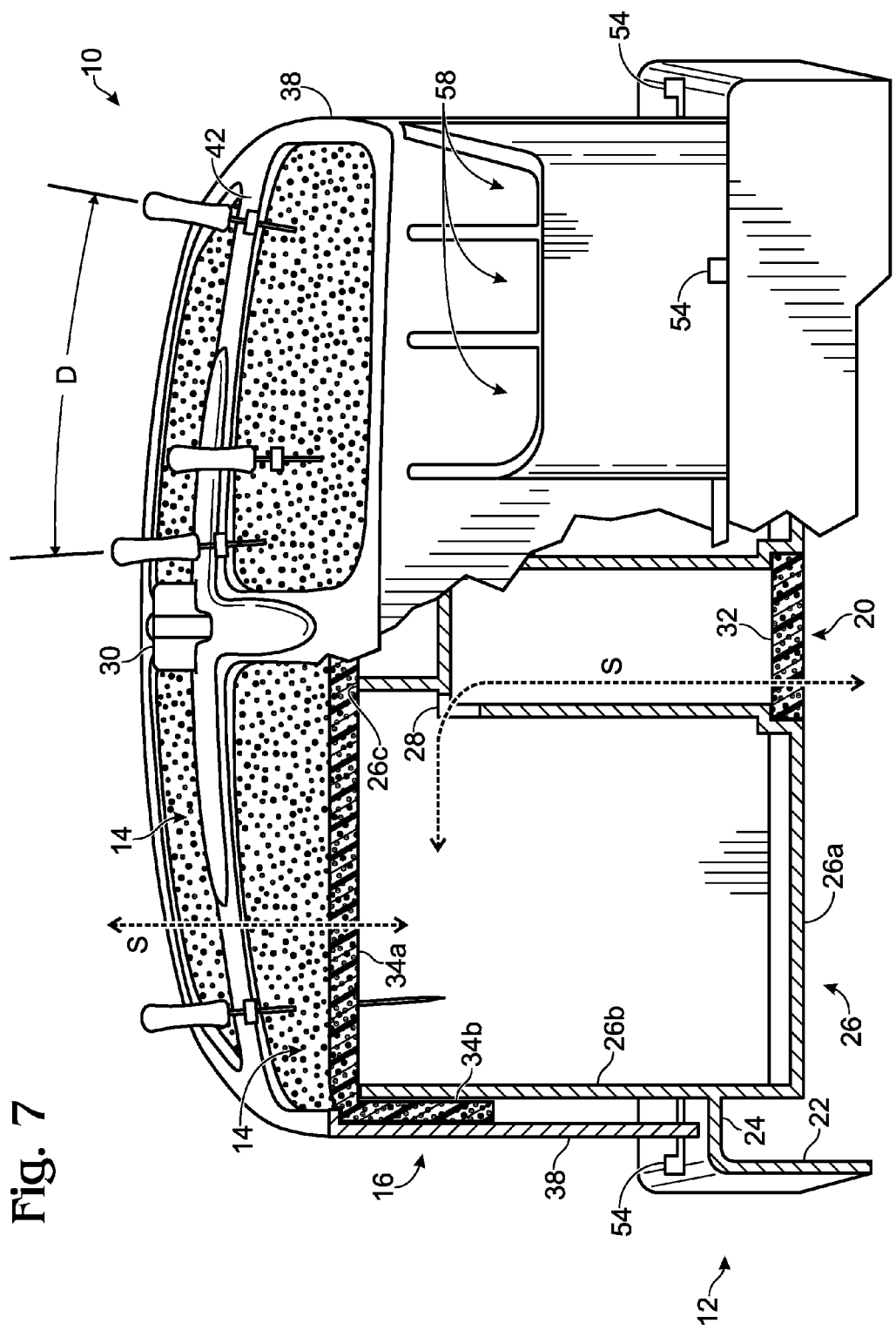
FIG. 7 shows a front view of aspects of the container for holding endodontic instruments shown in FIG. 1.

As shown in FIGS. 2 and 7, the base 12 is also configured to retain the foam filter 20 in a manner that forms a foam barrier between the vents 28 and the space outside the container. For example, the bottom 26a of each well 26 may protrude slightly below the substantially horizontal supports 24, thereby creating a space into which a properly dimensioned foam pad can be snugly engaged. The wells 26 further form a shelf 32 against which the foam pad may be positioned when fully engaged with the base, so as to ensure that the foam pad forms a complete foam barrier between the space outside the container, and the vents. It should be appreciated that other structure may also be used to retain the foam filter in a manner that forms a foam barrier between the vents and the space outside the container.

Figure 3:
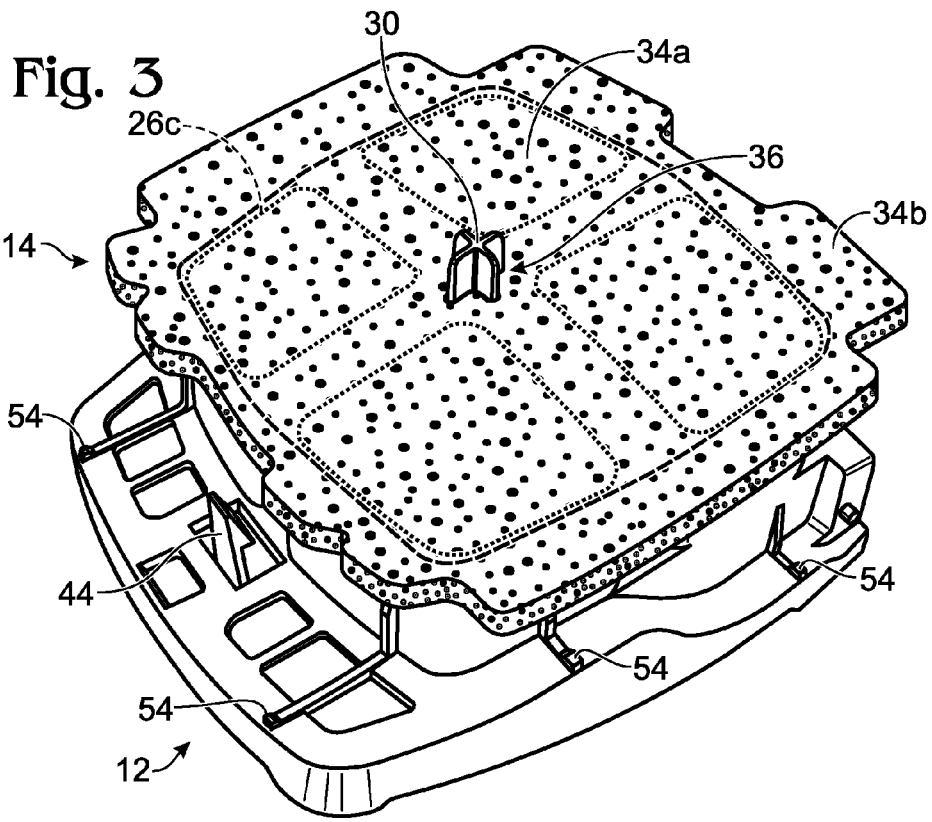
FIG. 3 shows a perspective view of a partially assembled container for holding endodontic instruments from FIG. 1, including a base, and a foam pad.
Figure 4:
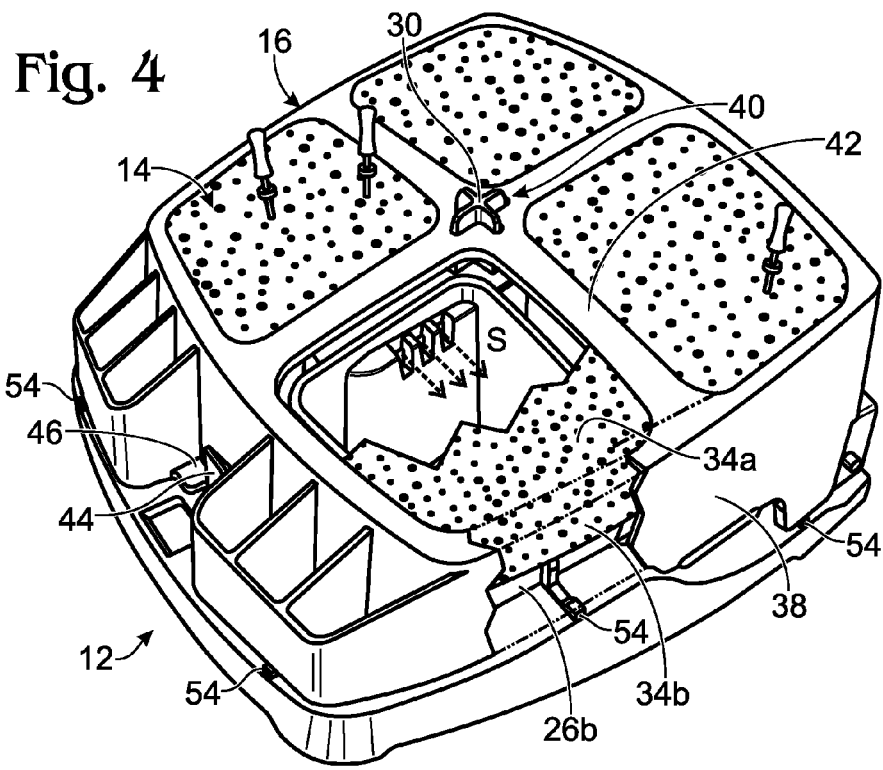
FIG. 4 shows a perspective view of a partially assembled container for holding endodontic instruments from FIG. 1, including a base, a foam pad, and a retainer.

FIGS. 3-4 show aspects of the foam pad 14, which functions to form a foam barrier over the open-ended tops of the instrument wells, and retains within the instrument wells the boring tips of endodontic instruments that have been inserted through the foam pad for storage and/or sterilization. The foam pad includes a first portion 34a, a second portion 34b and an engagement region 36. The first portion 34a is dimensioned to cover the open-ended top of each of the one or more wells, when the foam pad is properly aligned with respect to the base. The foam pad thus retains within the instrument wells the boring tips of endodontic instruments that have been inserted through the first portion for storage and/or sterilization. The second portion 34b extends beyond the top edges 26c of the wells, and thus is conformable around the top edges and against outside portions of the sidewalls. The second portion of the foam pad has an irregular shape so as to be flatly conformable against the outside portions of the sidewalls without interference from other of the container's structures. The engagement region 36 engages the guide 30 on the base 12 in a manner that properly aligns the foam pad with respect to the base.

The foam pad may be formed of any material that is consistent with its functions. For example, the foam pad may be formed of any material that is permeable to steam and substantially impermeable to biological contaminants. As discussed in more detail below, the material thus allows steam to pass into and out of the wells through the foam pad, while preventing some or all biological contaminants from passing into the wells through the foam pad. The foam pad may also be manufactured from any type of foam material having sufficient porosity and deformability to enable endodontic instruments to be repeatedly inserted into and/or through the material without compromising the foam pad's ability to form a foam barrier over the open-ended tops of the wells. For example, the foam pad may be manufactured from open-celled foam having a thickness of between about 0.125 to about 0.5 inches, and preferably of about 0.25 inches.

FIG. 4 shows aspects of the retainer 16, which tautly clamps the foam pad 14 to the base 12. The retainer includes sidewalls 38, an engagement region 40, and clamping bars 42. The retainer's sidewalls 38 are dimensioned to opposably surround the outer sidewalls 26b of the instrument wells (also shown in FIG. 7). The engagement region 40 engages the guide 30 on the base 12 in a manner that properly aligns the retainer with respect to the base. Thus, when the foam pad 14 is engaged with the base (as shown in FIG. 3 and described above), engaging the retainer with the base causes the retainer's sidewalls to bend the foam pad's second portion 34b over the top edges 26c of the instrument wells. The retainer's sidewalls 38 thereafter exert downward forces on the second portion 34b of the foam pad causing the first portion 34a to tauten over the open-ended tops of the instrument wells. When the retainer is fully engaged with the base, the retainer's sidewalls clamp the second portion against the outside portions of the instrument wells' sidewalls, and the retainer's clamping bars clamp the first portion 34a over the tops of the instrument wells.

The retainer 16 and/or base 12 may include a securing mechanism that releasably secures the retainer to the base. For example, the base may include a clip 44 that releasably engages retainer tab 46 when the retainer has been fully engaged with the base. The retainer may thus be secured to the base. Pulling back on the clip may disengage the clip from the tab, whereby a user may disengage the retainer from the base. It should be appreciated that the container may include any types of securing mechanism for releasably securing the retainer to the base, such as a latch, a bolt, a hook, etc.

Figure 5:
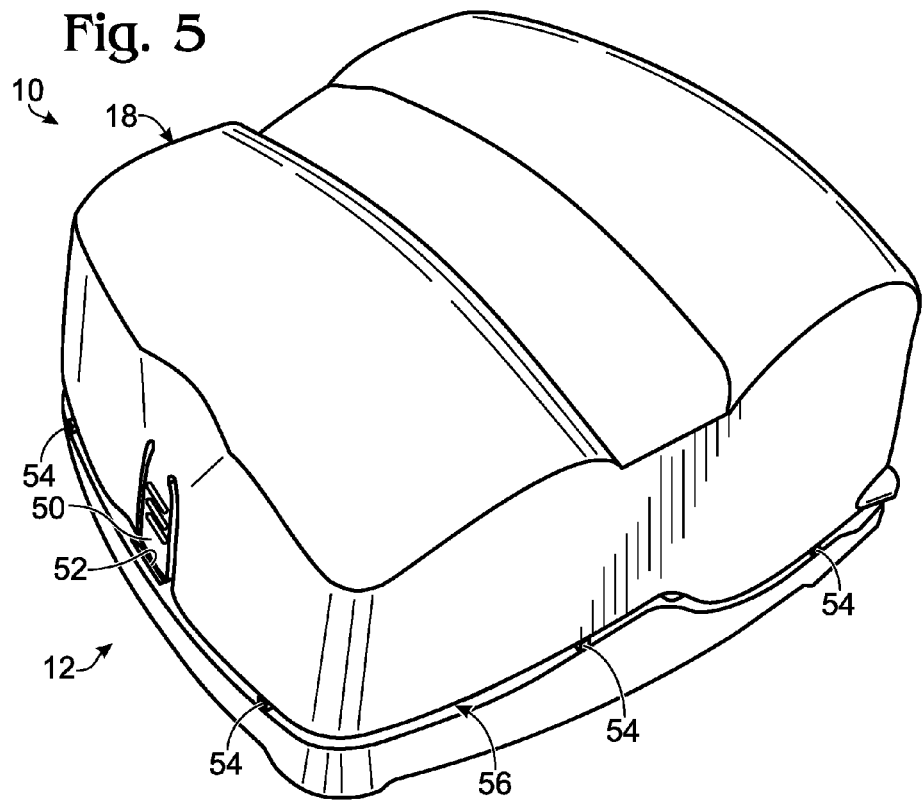
FIG. 5 shows a perspective view of a fully assembled container for holding endodontic instruments from FIG. 1.
Figure 6:
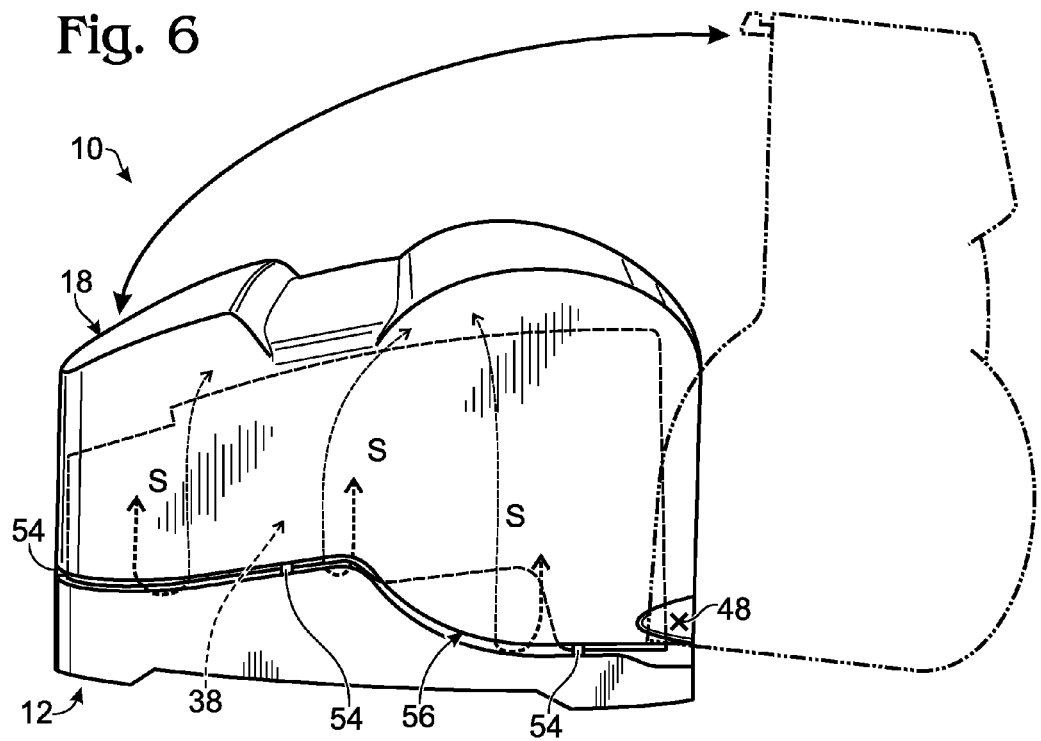
FIG. 6 shows a side view of a fully assembled container for holding endodontic instruments from FIG. 1.

FIGS. 5 and 6 show aspects of the lid 18, which functions to cover the foam pad 14 and any endodontic instruments retained by the foam pad. As best shown in FIG. 6, the lid is removably coupled to the base 12 by a hinge 48, and is pivotable between an open position (i.e. an open container) and a closed position (i.e. a closed container). In the closed position, the lid may form a space between the lid and the foam pad that is high enough to hold the handles of endodontic instruments that have been inserted through the foam pad. The lid and/or base may also include a securing mechanism that releasably secures the lid to the base when the lid is in the closed position. For example, the lid may include a latch 50 that releasably engages hole 52 when the lid has been closed, securing the lid to the base. Disengaging the latch from the hole may thereafter enable a user to open the lid. It should be appreciated that the container may include any type of releasable securing mechanism for securing the lid to the base when the lid is closed, such as a clip, a bolt, a hook, etc.

The lid 16 and base 12 is configured to ventilate the space between the lid and the foam pad. As shown in FIG. 6, the lid and/or base includes one or more spacers 54 that form a gap 56 between the lid and the base when the container is closed. The gap may surround the entire container to ensure sufficient and substantially uniform ventilation between the space outside the container and the space between the lid and the foam pad during a steam autoclaving process. Air passing into the closed container through the gap must then pass upward between the lid and the retainer's sidewalls 38 before reaching the foam pad.

FIGS. 2 and 7 show aspects of the foam filter 20. As described above, the foam filter is dimensioned to engage aspects of the base 12 in a manner that forms a foam barrier between the vents 28 and the space outside the container. The foam filter may also include tabs 60 that enable a user to grasp the filter during engagement and disengagement with the base. The foam filter may be made of any material that is permeable to steam and substantially impermeable to biological contaminants. For example, the foam filter may be manufactured from the same material as the foam pad.

FIG. 7 shows a front view of aspects of the container 10. The container is shown without the lid so as to show the internal components of the container. A portion of the container has also been cut-away through a vertical axis that is co-planar with one of the vents 28 to show the inside of a well 26. FIG. 7 will hereinafter be used to describe various functional aspects of the container.

The container is configured to hold endodontic instruments in a manner that enables a user to find and select the instruments during an endodontic procedure. As shown in FIG. 7, the retainer 16 secures the foam pad 14 to the base 12 in a manner that causes the foam pad to form a dome-like shape, and to have a downward slope from the back to the front of the container. The dome-like shape of the foam pad functions to widen the distance D between the handles of endodontic instruments that have been inserted through the foam pad with their longitudinal axes normal to the foam pad. Thus, the dome-like shape of the foam pad reduces crowding between the instruments' handles, and enables a user to more easily grasp the handles. The downward slope from back to front enables a user to more easily see the files being held by the container. Also as shown in FIG. 7, the container may include slots 58 for holding and organizing dental burrs, cotton balls, cotton swabs, files, or other small instruments that may be necessary for use during an endodontic procedure.

The container is configured to enable a user to sterilize endodontic instruments in a steam autoclave. During the steam autoclaving process, the fully assembled container is placed into an autoclaving chamber that is then filled with steam and pressurized. The pressure within the chamber forces the steam into the open spaces within the container that are permeable to steam. As described above and shown in FIG. 6, steam S enters the container through the gap 56 between the lid and the base, and passes upward between the lid and the retainer's sidewalls 38 before coming into direct contact with the foam pad 14. Steam also surrounds the outside of the container, coming into direct contact with the foam filter 20. Both the foam pad and the foam filter are permeable to steam, as described above. Steam S thus passes into the well 26 through the foam pad 14, or through the foam filter 20 and one or more vents 28, as shown in FIG. 7. The heat of the steam sterilizes the endodontic instruments, including the boring tips of the endodontic instruments that are retained by the foam pad within the well. After the container has been sterilized, the autoclave activates a drying cycle that depressurizes, vents and heats the autoclave chamber. During the drying cycle, the steam within the well 26 passes out of the container in the reverse direction from which it entered. The foam pad, foam filter, and surfaces of the container may for a time be saturated or covered with condensed water, which is dried by the autoclave or fresh air over time. The container containing the sterile endodontic instruments is then removed from the autoclave.

After sterilization, the container 10 prevents the endodontic instruments from being contaminated by biological contaminants, such as viruses, molds, fungi, bacteria, etc. Air enters the container in the same manner that steam enters the container as described above. Because air may carry biological contaminants, the container 10 provides several barriers to prevent these contaminants from reaching the sterilized endodontic files prior to their use in a procedure. For example, to prevent some or all biological contaminants from reaching the foam pad 14 within the closed container, the base 12 is shaped to position the foam pad a distance above the gap 56 (as shown in FIG. 6). Air entering the container through the gap must pass upwards between the narrow channel formed between the lid and the retainer's sidewalls 38 before coming into direct contact with the foam pad 14. The distance the air must travel through this narrow channel prevents some or all biological contaminants in the air from reaching the foam pad. In addition to the position of the foam pad relative to the gap, the container also retains the boring tips of endodontic instruments within a space that is blocked by foam barriers that are substantially impermeable to biological contaminants. Specifically, the foam pad forms a foam barrier over the open-ended top of the wells 26, and the foam filter forms a foam barrier between the air outside the container and the vents 28. As described above, both the foam pad and the foam filter are impermeable to some or all biological contaminants. Thus, the foam barriers prevent some or all biological contaminants from reaching the boring tips of the endodontic instruments.

The various components of the container 10 may be manufactured from any suitable material(s), and may have any size and shape consistent with their functions. The materials can be selected and/or finished to satisfy any suitable criteria, including strength, durability, appearance, and ease of use. For example, the container's components may be manufactured from autoclavable materials selected to permit sterilization of the endodontic instruments stored therein, such as high temperature plastics, ceramics, glass, foam, and/or metals, amongst others.

While the present invention has been particularly shown and described with reference to the foregoing depicted embodiments, those skilled in the art will understand that many variations may be made therein without departing from the spirit and scope of the invention as defined in the following claims. The description of the invention should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application. Where the claims recite "a" or "a first" element or the equivalent thereof, such claims should be understood to include incorporation of one or more such elements, neither requiring nor excluding two or more such elements.

We claim:

1. A container for holding endodontic instruments, comprising:
    a base having a well with a bottom and sidewalls extending upwardly from the bottom to an open-ended top;
    a foam pad configured to hold one or more endodontic instruments inserted through the pad, and dimensioned to enclose the open-ended top of the well;
    a retainer configured to clamp the foam pad over the open-ended top of the well so that the pad is tautly maintained in a holding position, whereby the foam pad is configured to hold at least a portion of an endodontic instrument within the well; and
    a lid coupled to the base, and movable between an open position and a closed position that covers the foam pad.

2. The container for holding endodontic instruments of claim 1, wherein the base includes a plurality of wells, the foam pad is dimensioned to enclose the open-ended tops of each of the wells, and the retainer is configured to clamp the foam pad over the open-ended tops of each of the wells so that the foam pad is tautly maintained in a holding position to hold at least a portion of an endodontic instrument within a selected one of the plurality of wells.

3. The container for holding endodontic instruments of claim 1, wherein the base includes a vent configured to enable steam to pass into the well.

4. The container for holding endodontic instruments of claim 3, further comprising a filter that engages the base in a manner that filters at least some of the contaminants from the steam before it passes through the base into the well.

5. The container for holding endodontic instruments of claim 4, wherein the filter is a foam insert permeable to steam, but impermeable to at least some of the contaminants present in the steam.

6. The container for holding endodontic instruments of claim 1, wherein the base includes a guide, and the foam pad includes an engagement region that engages the guide so as to align the foam pad to enclose the open-ended top of the well.

7. The container for holding endodontic instruments of claim 6, wherein the retainer includes an engagement region that engages the guide so as to align the retainer to clamp the foam pad over the open-ended top of the well.

8. The container for holding endodontic instruments of claim 1, wherein the base includes a securing mechanism that releasably secures the retainer to the base when the retainer has been used to clamp the foam pad over the open-ended top of the well.

9. The container for holding endodontic instruments of claim 1, wherein the lid includes a securing mechanism that releasably secures the lid to the base when the lid is in the closed position.

10. The container for holding endodontic instruments of claim 1, wherein the base includes a spacer that substantially creates a space between the base and the lid when the lid is in the closed position, and whereby the space enables steam to pass therethrough.

11. The container for holding endodontic instruments of claim 1, wherein the foam pad is an open celled foam having a thickness of between 0.125 to 0.500 inches thick.

12. The container for holding endodontic instruments of claim 1, wherein the container is autoclavable.

13. A container for holding endodontic instruments, comprising:
    a base having a well with a bottom and sidewalls extending upwardly from the bottom to an open-ended top;
    a foam pad configured to hold one or more endodontic instruments inserted through the pad, and dimensioned to have a first portion that encloses the open-ended top of the well, and a second portion that conforms around a top portion of the sidewalls and against an outside portion of the sidewalls;
    a retainer configured to secure the foam pad to the well, wherein the first portion of the foam pad is tautened over the open-ended top of the well, and the second portion of the foam pad is clamped by the retainer against the outside portions of the sidewalls, and wherein the first portion is configured to hold at least a portion of an endodontic instrument within the well; and a lid coupled to the base, and movable between an open position and a closed position that covers the foam pad.

14. The container for holding endodontic instruments of claim 13, wherein the base includes a vent configured to enable steam to pass into the well.

15. The container for holding endodontic instruments of claim 13, wherein:

the base includes a guide;

the foam pad includes an engagement region that engages the guide so as to align the first portion into a position to enclose the open-ended top of the well, and the second portion into a position to conform around the top portion of the sidewalls and against the outside portion of the sidewalls; and the retainer includes an engagement region that engages the guide so as to align the retainer to clamp the second portion against the top and the outside portions of the sidewalls.

16. The container for holding endodontic instruments of claim 13, wherein the base includes a securing mechanism that releasably secures the retainer to the base when the retainer has been used to secure the foam pad to the well.

17. The container for holding endodontic instruments of claim 13, wherein the lid includes a securing mechanism that releasably secures the lid to the base when the lid is in the closed position.

18. The container for holding endodontic instruments of claim 13, wherein the base includes a spacer that substantially creates a space between the base and the lid when the lid is in the closed position, and whereby the space enables steam to pass therethrough.

19. The container for holding endodontic instruments of claim 13, wherein the foam pad is an open celled foam having a thickness of between 0.125 to 0.500 inches thick.

20. The container for holding endodontic instruments of claim 13, wherein the container is autoclavable.

21. A container for holding endodontic instruments, comprising:

a base including a plurality of wells that each have a bottom and sidewalls extending upwardly from the bottom to an open-ended top;

a foam pad configured to hold one or more endodontic instruments inserted through the pad, and dimensioned to enclose the open-ended tops of each of the wells;

a retainer configured to clamp the foam pad over the open-ended tops of each of the wells so that the pad is tautly maintained in a holding position, whereby the foam pad is configured to hold at least a portion of an endodontic instrument within a selected one of the plurality of wells; and a lid coupled to the base, and movable between an open position and a closed position that covers the foam pad;

wherein the base includes a plurality of vents configured to enable steam to pass into each of the plurality of wells.

* * * * *